United States Patent [19]

Soni

[11] Patent Number: 4,593,681

[45] Date of Patent: Jun. 10, 1986

[54] STABILIZING DEVICE FOR USE IN ARTHROSCOPIC AND ENDOSCOPIC SURGERY

[76] Inventor: Prasanna L. Soni, 4717 Greenbriar Sq. N.E.,, Canton, Ohio 44714

[21] Appl. No.: 692,429

[22] Filed: Jan. 18, 1985

[51] Int. Cl.$^4$ ............................................. A61B 1/00
[52] U.S. Cl. .............................. 128/4; 128/DIG. 26; 604/174
[58] Field of Search ............... 128/3, 4, 5, 6, 7, 303 B, 128/DIG. 26; 604/174, 180

[56] References Cited

U.S. PATENT DOCUMENTS 2,898,917  8/1959  Wallace .............................. 604/180
4,353,369  10/1982  Muetterties et al. ............ 604/180 X

FOREIGN PATENT DOCUMENTS 1184139  2/1959  France ....................... 128/DIG. 26

Primary Examiner—William H. Grieb

Attorney, Agent, or Firm—Sand & Hudak Co.

[57] ABSTRACT

A device which stabilizes the sheath of an endoscope or arthroscope during surgery. The device is a relatively thin, flat, flexible plate of plastic material and is adapted to be placed against a patient's body at the area where penetration is made by the scope sheath. The plate is formed with a predetermined sized central hole and the sheath is slidably inserted through the hole and has an interference fit with the surrounding plate material. The plate provides a stable base for the scope to be slidably moved with respect to the plate to adjust the depth of penetration. The plate preferably has a bow or generally figure-eight configuration which provides sufficient surface area at both ends of the plate to provide a stable base for the scope while permitting other surgical instruments to be inserted into the patient's body closely adjacent the scope due to the concavity of the plate sides. Various mechanisms can be mounted in the central plate hole to accommodate various sizes of scope sheaths.

7 Claims, 11 Drawing Figures

STABILIZING DEVICE FOR USE IN ARTHROSCOPIC AND ENDOSCOPIC SURGERY

TECHNICAL FIELD

The invention relates to surgical devices and in particular to a device for use in arthroscopic and endoscopic surgery. More particularly, the invention relates to a device which provides a stable base for the sheath of the endoscope or arthroscope during surgery.

BACKGROUND ART

The use of arthroscopic and endoscopic surgery for performing numerous types of surgical procedures has increased considerably over the past several years. Such surgery enables various procedures to be performed within the body without requiring large incisions heretofore required to reach the effected area. In such surgery the principle instrument used is an endoscope or arthrosope. Such instruments usually include a cylindrical shaped tube or scope sheath, sometimes referred to as a cannula, which is formed of stainless steel and which is attached to and extend outwardly from appropriate electronic components attached to the rear end of the sheath. This equipment consists of a television device or microscope using fiber optics to provide the surgeon with a view of the interior of the patient's body on which the surgery is being performed. The sheath penetrates the body or limb of the patient adjacent the effected area through a small incision formed in the body. This scope sheath is attached to and is movable with the hand held and manipulated equipment which provides the visual picture of the effected area within the patient's body. Other surgical instruments then are inserted into the body through the hollow interior of the scope sheath and penetrate to the effected area to enable the surgeon to perform the desired procedure on the effected area while viewing the same through an eyepiece or television monitor connected to the endoscope or arthroscope.

One problem that occurs in such surgery is that it is difficult for the surgeon to maintain the scope absolutely still during the entire surgery procedure since the scope usually is supported entirely by the surgeon's hand. During the course of the surgery, the depth of penetration of the scope may vary as well as its lateral position within the body due to the difficulty of maintaining the scope in the desired position because of the strain on the surgeon's hand. Various types of elaborate and bulky mechanisms have been designed to position and support the scope at the desired position in an attempt to eliminate or reduce such unwanted movement and strain on the surgeon's hand and to provide a constant steady field of vision to the surgeon. However, such equipment is relatively bulky and expensive and interferes with the use of the other surgical instruments which are inserted into the patient's body closely adjacent to the location of penetration of the endoscope sheath.

During the course of the surgery, it may become necessary to adjust the penetration of the scope sheath to provide a different field of view to the surgeon, and such movement is difficult with existing stabilizing equipment. Also, such existing equipment must be maintained in a completely sterile and sanitary condition for each surgical procedure which increases further the cost of the surgery and maintainence of the equipment.

Therefore, the need has existed for an improved stabilizing device for use in arthroscopic and endoscopic surgery which is effective, inexpensive, and easily sterilized which assists the surgeon to maintain the scope sheath in a fixed position and which enables changes in the depth of scope penetration during the course of the surgical procedures. There is no known device of which I am aware which achieves these advantages prior to my invention.

DISCLOSURE OF THE INVENTION

Objectives of the invention include providing an improved stabilizing device for use in arthroscopic and endoscopic surgery which is formed from an extremely inexpensive flat, thin plate of plastic material having a bow or figure-eight configuration having a central opening of a predetermined diameter to provide an interference fit with the sheath of a scope inserted therein, and in which the interference fit provides for manual movement of the scope when desired by the surgeon to change the depth of penetration thereof, and which relieves much of the strain on the surgeon's hand while maintained in position during surgery. Another objective is to provide such a stabilizing device in which the plate is formed of a molded flexible F.D.A. approved plastic material, such as low density polyurethane, and in which the device preferably is packaged in sanitary packets and is intended to be easily disposed of after use since it can be produced and packaged at a very low cost.

A further objective of the invention is to provide such a stabilizing device in which the plate has a bow or figure-eight configuration which provides two sufficiently large surface areas at opposite ends of the plate to provide a stable base which is pressed against the patient's body by the surgeon or assistants, with the concavity of the plate sides permitting other surgical instruments to be positioned closely adjacent to the scope, and in which the plate may be rotated on the scope sheath after the sheath is positioned within the body to eliminate interference with other surgical instruments. Another objective is to provide such a stabilizing device in which various types of adjustable opening-retention mechanisms may be mounted on the plate to accommodate a range of diameter sizes of endoscope sheaths. A still further objective is to provide such a stabilizing device which can be mass produced inexpensively and packaged in sanitary packets for disposal after use in a surgical procedure, which device is lightweight and flexible so as to conform to the contour of the patient's body in the area of surgery, which provides a stable base for the scope and prevents pistoning of the scope during surgery, and which eliminates difficulties existing with prior stabilizing devices, satisfies need and obtains new results in the art.

These objectives and advantages are obtained by the improved stabilizing device of the invention, the general nature of which may be stated as including a plate formed of a flexible plastic material adapted to be placed against a patient's body at an area where the sheath of a scope penetrates the body; and opening means formed in the plate for receiving and holding the sheath extending therethrough during surgery.

BRIEF DESCRIPTION OF THE DRAWINGS

A preferred embodiment of the invention, illustrative of the best mode in which applicant has contemplated applying the principles, is set forth in the following description and is shown in the drawings and is particularly and distinctly pointed out and set forth in the appended claims.

Similar numerals refer to similar parts throughout the drawings.

BEST MODE FOR CARRYING OUT THE INVENTION

Figure 1:
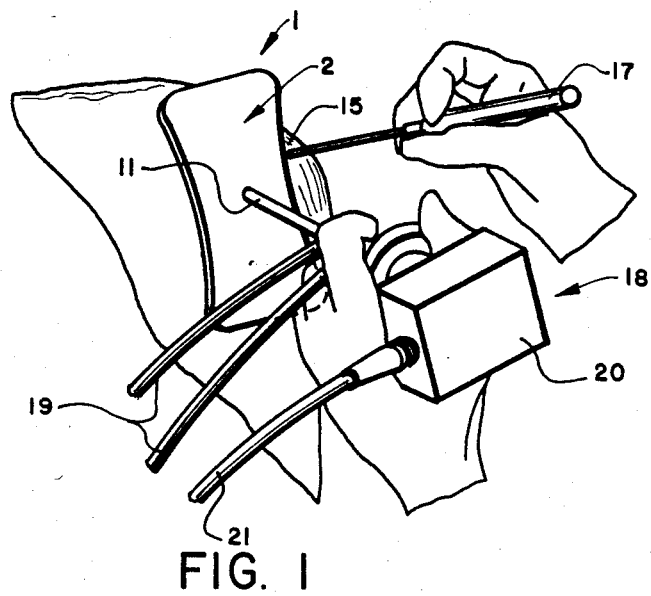
FIG. 1 is a perspective diagrammatic view showing the improved stabilizing device in use during surgery.
Figure 5:
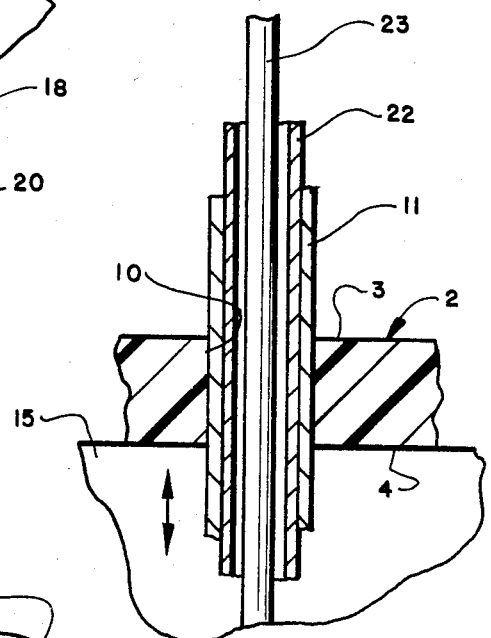
FIG. 5 is an enlarged fragmentary sectional view of portions of a scope being used with the stabilizing device.
Figure 2:
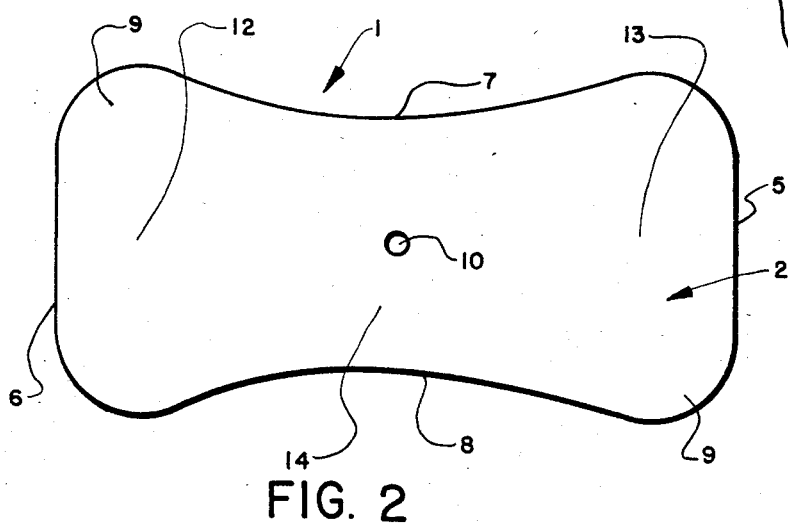
FIG. 2 is an enlarged plan view of the stabilizing device of FIG. 1.
Figure 3:
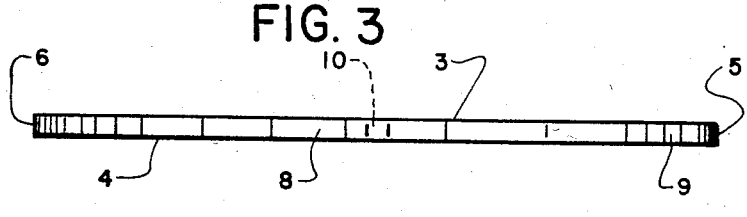
FIG. 3 is a side view of the device of FIG. 2.
Figure 4:
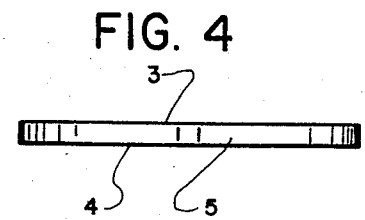
FIG. 4 is an end view of the stabilizing device of FIGS. 2 and 3.

The improved stabilizing device is indicated generally at 1, with the preferred embodiment having shown particularly in FIGS. 2, 3, and 4. Device 1 is shown in FIGS. 1 and 5 in use during a usual type of arthroscopic or endoscopic surgery. Device 1 includes a relatively flat, thin plate 2 preferably formed of flexible plastic material, such as low density polyurethane of the type approved by the Food & Drug Administration (FDA).

Plate 2 preferably has a bow or figure-eight configuration as shown in FIG. 2 defined by a pair of opposed smooth flat surfaces 3 and 4, a pair of spaced parallel preferably straight end edges 5 and 6, and a pair of concave longitudinally extending side edges 7 and 8. This configuration provides two broad surface areas 12 and 13 which extend outwardly from a smaller central area 14. End edges 5 and 6 are joined with side edges 7 and 8 by rounded corners 9. This particular configuration of plate 2 may vary if desired although the concave shape of side edges 7 and 8 enables auxillary surgical instruments as shown in FIG. 1, to be inserted into a patient's body close to the location of the endoscope or arthroscope as described more fully below.

A circular shaped hole 10 is formed in the center of plate 2 and extends through the plate in a perpendicular direction with respect to surfaces 3 and 4. Hole 10 has a predetermined size diameter so as to be complementary to the outside diameter of a particular sized scope sheath or cannula 11 with which device 1 will be used. The diameter of hole 10 is sized to provide an "interference fit" with sheath 11 whereby the sheath will extend through hole 10 in such a manner to provide a sliding frictional relationship with the surrounding plate material. This interference fit provides sufficient friction and tightness between the plate and sheath whereby the sheath is held sufficiently tight to relieve the stress and strain on the surgeon's hand yet enables the sheath to be slid transversely through plate 2 by applying a predetermined amount of pressure or force on the sheath. The fit will not permit a loose sliding engagement between the sheath and plate which will defeat the purpose of device 1, that is, the stabilizing of the scope sheath once placed in the desired position.

A preferred size of plate 2 will have a longitudinal length of approximately 4.5 inches and a width of 2.25 inches whereby the length is approximately twice the width of the plate. Also, the thickness of plate 2 may vary depending upon the particular type of plastic material used in its construction with a preferred range of thickness being between 0.05 inches and 0.10 inches. However, a satisfactory plate could be formed thicker or thinner than the preferred range set forth above without departing from the concept of the invention. Preferably, sufficient flexibility is inherent in the plate so that the plate can be formed slightly to match the contour of the portion of the patient's body with which it is being used.

The particular use of improved stabilizing device 1 is shown particularly in FIGS. 1 and 5. One of the smooth flat surfaces 3 or 4 is placed against a knee 15, or other position on the patient, so that broad areas 12 and 13 of the plate lie against and along the patient's knee. Areas 12 and 13 provide a sufficiently broad base when pressed against the knee to stabilize a sheath or cannula 11 of an endoscope or arthroscope. Areas 12 and 13 also provide surfaces whereby surgical assistants or the surgeon can manually press the plate against the patient's knee to further stabilize the plate when placed in the desired position. As shown in FIG. 1, the concavity of plate side edges 7 and 8 enables another surgical instrument or probe 17 to be positioned closely adjacent sheath 11 without interference from plate 2.

During the course of a usual type of scope surgery in which plate 2 will be used, the position or penetration depth of scope sheath 11 can be adjusted easily by exerting an inward or outward pressure on the endoscope or arthroscope while holding plate 2 in position against the knee. This enables the scope sheath to slide through hole 10 (FIG. 5) until the desired depth of penetration is reached. Referring to FIG. 1, an endoscope or arthroscope indicated generally at 18, preferably will have a pair of fluid lines 19 connected thereto for supplying a salene solution into the knee. Sheath 11 is mounted on a fiber optic telescope or television unit 20 which is connected to a source of power by an electric cord 21 to provide the surgeon with a visual inspection of the knee interior either through an attached eyepiece or on a closely adjacent television screen (not shown). A trocar 22 may be slidably inserted through the interior of sheath 11 and usually will have a sharp end which penetrates into the desired area of the knee. A telescope tube 23 then may be slidably received within trocar 22 as shown in FIG. 5. However, these instruments may vary without effecting the concept of the invention.

If another secondary incision is required in the patient's knee for insertion of another probe 17, plate 2 can be rotated easily about inserted sheath 11 without disturbing the sheath's position and depth of penetration. This facilitates the use of the stabilizing device without interferring with other surgical instruments that may be required to penetrate the patient's knee in close proximity to the endoscope sheath.

Device 1 due to its simplicity can be mass produced in large quantities at a relatively low cost, and can be individually packaged after being sanitized in sanitary wrappings, whereby the device can be removed from the package in the operating room at the time of the surgery for immediate use by the surgeon. Upon completion of the surgery, device 1 preferably is discarded and need not be reused since the unit cost is low which eliminates any subsequent sterilization and storage problems.

Figure 6:
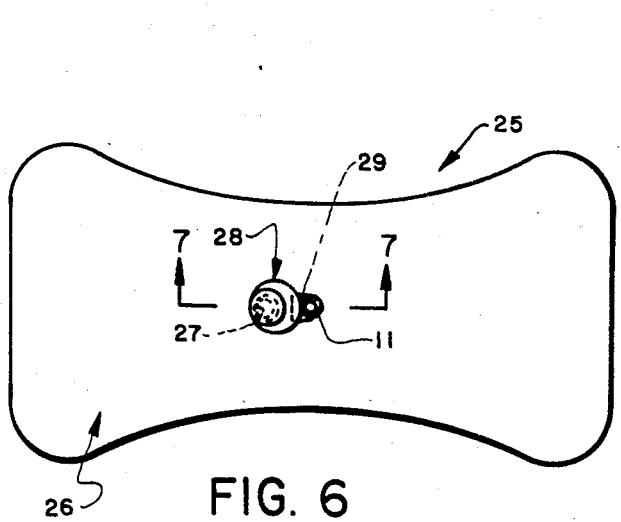
FIG. 6 is a top plan view with the scope shown in section, of a modified form of the improved stabilizing device having an adjustable scope sheath opening and cam retaining mechanism.
Figure 7:
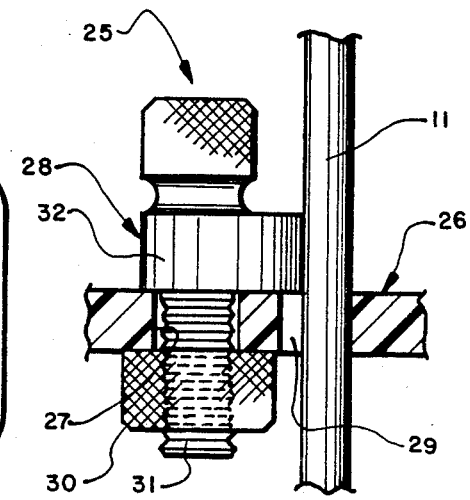
FIG. 7 is a greatly enlarged fragmentary sectional view of the cam retaining mechanism taken on line 7—7, FIG. 6.

A modified form of the improved stabilizing device is indicated generally at 25 and is shown in FIGS. 6 and 7. Modified device 25 is similar to device 1 except for the means by which scope sheath 11 is engaged or communicates with the stabilizing plate. Stabilizing device 25 includes a plate 26 which is similar in most respects to plate 2 except that a cam actuated retention mechanism indicated generally at 28, is mounted within a hole 27 formed in the center of plate 26 for engagement with sheath 11 which is adapted to extend through a closely adjacent tapered hole 29. Retention mechanism 28 includes a nut 30 preferably having a knurled outer surface which is threadably engaged with a camming stud 31 which includes an eccentric camming member 32.

Scope sheath 11 is inserted through tapered hole 29 and retention cam 28 is rotated until eccentric cam member 32 is engaged with sheath 11 securing it within hole 29 to prevent its free sliding movement therein. Nut 30 then is tightened to secure cam member 32 in its adjacent position against sheath 11. Cam member 32 may be pressed against sheath 11 with sufficient force to prevent any sliding movement through plate hole 29 requiring loosening of nut 30 to adjust the penetration depth of sheath 11, or it may be pressed against sheath 11 with sufficient force to provide the sliding adjustable engagement therewith similar to the interference fit within hole 10 of plate 2. This interference fit will permit adjustment of sheath 11 without manipulation of nut 30.

Figure 8:
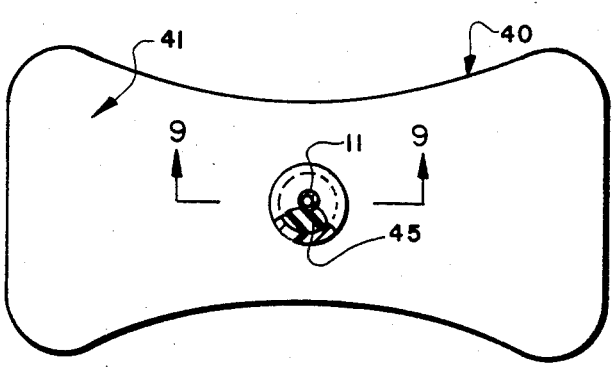
FIG. 8 is a top plan view with the scope shown in section, of the improved stabilizing device having a collapsible bushing scope sheath retaining and opening forming mechanism.
Figure 9:
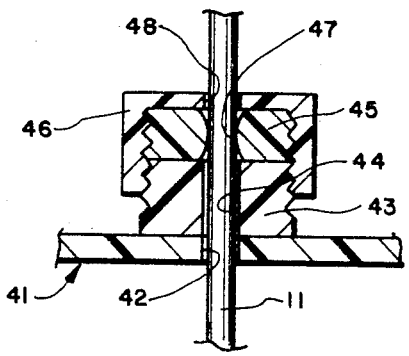
FIG. 9 is a greatly enlarged fragmentary sectional view taken on line 9—9, FIG. 8.

A further modification of improved stabilizing device 1 is shown in FIGS. 8 and 9 and is indicated generally at 40. Device 40 includes a plate 41 similar to plate 2 of device 1 having a central hole 42 formed therein which is larger than the diameter of the scope sheath to be used with device 40. An externally threaded annular shaped stud 43 preferably formed of plastic, is secured to one surface of plate 41 and has a central hole 44 formed therein which aligns with plate hole 42. An annular-shaped soft flexible bushing 45 having a central opening 47 is clamped against the top annular surface of stud 43 by an internally threaded plastic end cap 46. End cap 46 is formed with a central hole 48 which aligns with bushing hole 47, stud hole 44 and plate hole 42.

Upon the axial advancement of end cap 46 along the external threads of stud 43 bushing 45 axially compresses and expands radially against sheath 11 to provide either a tight clamping engagement with sheath 11 or the desired interference fit therebetween. The advancement of cap 46 toward the surface of plate 41 determines the amount of sliding friction or clamping force between bushing 45 and sheath 11.

Figure 10:
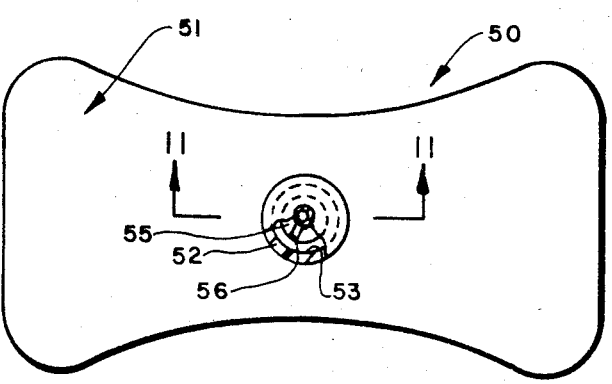
FIG. 10 is a top plan view with the scope shown in section of the stabilizing device having a flexible collet scope sheath retaining and opening forming mechanism.
Figure 11:
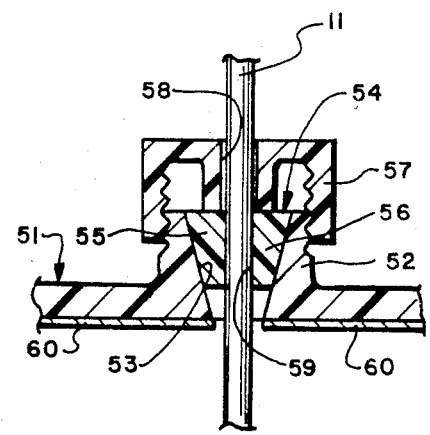
FIG. 11 is a greatly enlarged fragmentary sectional view taken on line 11—11, FIG. 10.

Another modified stabilizing device is shown in FIGS. 10 and 11 and is indicated generally at 50. Modification 50 is similar in most respects to device 1, 25 and 40 described above in that it includes a flat, thin flexible plastic plate 51 formed with a central externally threaded central boss 52 having a downwardly inwardly tapered hole 53 formed therein. A usual type of flexible collet indicated generally at 54, which is formed with a series of alternating hard and soft plastic segments 55 and 56 respectively, is forced into tapered hole 53 by an internally threaded end cap 57. Cap 57 has a central opening 58 which aligns with central opening 59 of collet 54.

As in device 40 described above, the axial advancement of end cap 57 toward plate 51 by the threaded engagement with boss 52 axially compresses soft collet segments 45 expanding them radially inwardly against sheath 11 to provide a tight clamping engagement or interference fit with the sheath. Again, the extent of the axial advancement of end cap 57 determines the amount of clamping force exerted by the soft collet segments against sheath 11.

A strip of pressure sensitive adhesive 60 is shown attached to the bottom surface of plate 51 for temporarily attaching the plate to a patient's body for certain types of surgical procedures. For example, the plate can be pressed against the back or other relatively flat portion of the patient's body to increase the stability provided by the device. This adhesive strip may be used on plate 2, 26 and 41 to achieve this same result, if desired.

Embodiments 25, 40 and 50 described above enable the stabilizing plates to be used with various sizes or diameters of sheath scopes instead of requiring the plate hole to match the diameter of the sheath to achieve the desired interference fit therebetween. These modified stabilizing devices having the various types of retention and adjustable opening means mounted in the center thereof are desirable when the plates are to be used with different size sheaths and not one particular size as in plate 2.

Retention mechanism 28 is removably attached to plate 26 and may be reusable with different plates if desired since it is readily detached from the plate in contrast to the adjustable opening forming and retention mechanisms of devices 40 and 50 which are formed as part of the plate. Preferably modified devices 25, 40 and 50 are not disposable and are intended for reuse in various arthroscopic surgery procedures after sterilizing the same between procedures.

Various other types of adjustable opening forming and sheath retention mechanisms may be formed as a part of the stabilizing plate or attached thereto than the three examples shown in FIGS. 6–11 and described above without effecting the concept of the invention. These three devices are examples of different mechanisms whereby the device may be used for a range of sheath sizes instead of being matched to a particular size sheath as device 1 of FIGS. 1–5.

The improved stabilizing device provides an extremely inexpensive, sanitary device which is ergonomically designed to provide greater stability of the scope during operative arthroscopy or endoscopy which prevents pistoning of the scope, and which provides a stable base for the scope to relieve or materially reduce the stress and strain on the surgeon during surgery. Furthermore, the device when providing the interference fit with the scope sheath can be rotated to achieve the most efficient location on the patient's body and to prevent interference with other surgical instruments, which due to the concave configurations of the plate side edges can be located closely adjacent to the scope sheath without effecting the broad stabilizing areas of the plate. The device also can be formed of inexpensive FDA approved plastic material enabling them to be disposable.

Accordingly, the improved stabilizing device is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries, and principles of the invention, the manner in which the improved stabilizing device for use in arthroscopy and endoscopy surgery is constructed and used, the characteristics of the device, and the advantageous, new and useful results obtained; the new and useful structures, elements, arrangements, parts, and combinations, are set forth in the appended claims.

What is claimed is:

1. A device for stabilizing a sheath of an endoscope or arthroscope during surgery including a plate formed of a flexible plastic material adapted to be placed against the patient's body at an area where the sheath penetrates the body; a camming stud rotatably mounted on the plate; and a tapered hole formed in the plate adjacent the camming stud for receiving the sheath extending therethrough during surgery with the camming stud being rotatable into engagement with the sheath to retain and hold said sheath within said tapered hole.

2. A device for stabilizing a sheath of an endoscope or arthroscope during surgery including a plate formed of a flexible plastic material adapted to be placed against the patient's body at an area where the sheath penetrates the body; opening means formed in the plate for receiving and holding the sheath extending therethrough during surgery; said opening means including an adjustable opening forming member mounted on the plate having an externally threaded projection, an end cap threadably engaged with said projection, and a soft deformable member located between the projection and end cap and having a central opening adapted to receive the sheath therein whereby axially movement of the end cap on the projection compresses the deformable member expanding it into clamping engagement with the sheath.

3. The stabilizing device defined in claim 2 in which the plate is generally flat and sufficiently thin to provide some flexibility thereto; and in which said plate has a generally figure-eight configuration.

4. The stabilizing device defined in claim 3 in which the longitudinal length of the plate is approximately twice its maximum width.

5. The stabilizing device defined in claim 4 in which the plate has a longitudinal length of approximately 4½ inches and a maximum width of approximately 2¼ inches.

6. The stabilizing device defined in claim 3 in which the plate is formed of a low density polyurethane with a thickness within a range of between 0.05 and 0.10 inches.

7. The stabilizing device defined in claim 2 in which a pressure sensitive adhesive is applied to a surface of the plate for removably attaching the plate to the body of a patient.

* * * * *